United States Patent [19]

Kinoshita

[11] Patent Number: 4,552,130
[45] Date of Patent: Nov. 12, 1985

[54] AIR AND LIQUID SUPPLYING DEVICE FOR ENDOSCOPES

[75] Inventor: Kunio Kinoshita, Tokyo, Japan

[73] Assignee: Olympus Optical Co., Ltd., Tokyo, Japan

[21] Appl. No.: 583,428

[22] Filed: Feb. 24, 1984

[30] Foreign Application Priority Data

Mar. 1, 1983 [JP]  Japan ................................ 58-33574

[51] Int. Cl.[4] ............................................. A61B 1/00
[52] U.S. Cl. .................................................... 128/4
[58] Field of Search .................... 128/4, 5, 6, 7, 8, 10, 128/11

[56] References Cited

U.S. PATENT DOCUMENTS

| | | | |
|---|---|---|---|
| 4,261,343 | 4/1981 | Ouchi et al. | 128/4 |
| 4,311,134 | 1/1982 | Mitsui et al. | 128/6 |
| 4,325,362 | 4/1982 | Ouchi et al. | 128/4 |
| 4,325,368 | 4/1982 | Kaemmerer . | |
| 4,489,712 | 12/1984 | Ohshimi | 128/6 |

FOREIGN PATENT DOCUMENTS

| | | | |
|---|---|---|---|
| 0055394 | 7/1982 | European Pat. Off. | 128/4 |
| 0071058 | 2/1983 | European Pat. Off. . | |
| 2462897 | 2/1981 | France . | |

Primary Examiner—William H. Grieb

[57] ABSTRACT

An air and liquid supplying device has an air pump, a first feed liquid tank containing a first liquid, and a first selector valve connected to a feed air passage and a feed liquid passage of an endoscope. The pump is connected to the first selector valve by a air supply passage and the liquid tank is connected to the valve by a liquid supply passage. The air supply passage is connected to the tank through a pressurizing passage. The first valve is shifted between a first position where air from the pump is fed into the feed air passage and a second position where the first liquid is fed into the feed liquid passage. A second feed liquid tank containing a second liquid is connected to the air supply passage between the pump and the pressurizing passage. A second selector valve is connected to the air supply passage and shifted between a first position where air from the pump is fed into the air supply passage, and a second position where the second liquid is fed into the air supply passage.

11 Claims, 8 Drawing Figures

AIR AND LIQUID SUPPLYING DEVICE FOR ENDOSCOPES

BACKGROUND OF THE INVENTION

The present invention relates to an air and liquid supplying device for an endoscope, and more specifically to an air and liquid supplying device capable of feeding a liquid into a feed air passage of an endoscope to wash the passage.

In general, when using an endoscope, filthy things, such as mucus, are liable to stick to a monitoring window at the distal end of the insert section of the endoscope, thereby narrowing the field of vision for observation. In order to ensure a satisfactory observation, therefore, water is supplied to a nozzle at the distfal end of the insert section through the feed liquid passage of the endoscope, and is then sprayed on the surface of the monitoring window to wash the same. Air is then delivered to the nozzle through a feed air passage to remove any water drops remaining on the monitoring window.

Recently, in hospitals, infections from endoscopes have become a problem. To avoid such an infection, the insert section of an endoscope, after use, is conventionally immersed in an antiseptic solution, or the antiseptic solution is passed through a forceps channel to disinfect the interior of the channel. Also, the feed liquid passage, which, like the forceps channel, can easily be supplied with water or medical fluid, is conventionally washed and disinfected.

In order to securely disinfect the whole structure of an endoscope, the interior of the feed air passage also needs to be washed and disinfected, since some filth may possibly flow backward from the nozzle into the feed air passage. Owing to the structural conditions of the endoscope, however, it is particularly hard to wash or disinfect the feed air passage. Accordingly, the feed air passage is usually left unwashed and undisinfected after use, and so the filth attached to the feed air passage can possibly cause an infection.

SUMMARY OF THE INVENTION

The present invention is contrived in consideration of these circumstances, and is intended to provide an air and liquid supplying device for an endoscope simple in construction and capable of washing and disinfecting a feed air passage of the endoscope by feeding a liquid into the passage.

According to an aspect of the invention, there is provided an air and liquid supplying device which comprises: an air pump; a first feed liquid tank containing a first liquid; first switching means connected to a feed air passage and a feed liquid passage of an endoscope; connecting means including an air supply passage connecting the pump and the first switching means, a pressurizing passage diverging from the air supply passage and communicating with the first feed liquid tank, and a liquid supply passage connecting the first feed liquid tank and the first switching means; the first switching means being capable of being shifted between a first position where the air supply passage and the feed air passage are connected so that air from the pump is fed into the feed air passage, and a second position where the feed air passage is cut off and the liquid supply passage and the feed liquid passage are connected so that the first liquid is fed into the feed liquid passage; a second feed liquid tank containing a second liquid and connected to the air supply passage between the pump and the pressurizing passage; and second switching means connected to the air supply passage between the second feed liquid tank and the pressurizing passage, and adapted to switch the device between the air supply to the air supply passage and the second liquid supply to the air supply passage.

According to the device described above, the air and the first liquid can be fed into the feed air passage and the feed liquid passage, respectively, by shifting the first switching means. The second liquid can be fed into the feed air passage via the air supply passage by shifting the second switching means. Thus, according to the present invention, the second liquid may be fed into the feed air passage with use of a simple construction, and the feed air passage can be washed and disinfected by using an antiseptic solution for the second liquid.

BRIEF DESCRIPTION OF THE DRAWINGS

FIGS. 1 to 4 show an air and liquid supplying device according to a first embodiment of the present invention, in which

DETAILED DESCRIPTION OF THE PREFERRED EMBODIMENT

Preferred embodiments of the present invention will now be described in detail with reference to the accompanying drawings.

Referring first to FIGS. 1 to 4, the first embodiment will be described.

Figure 1:
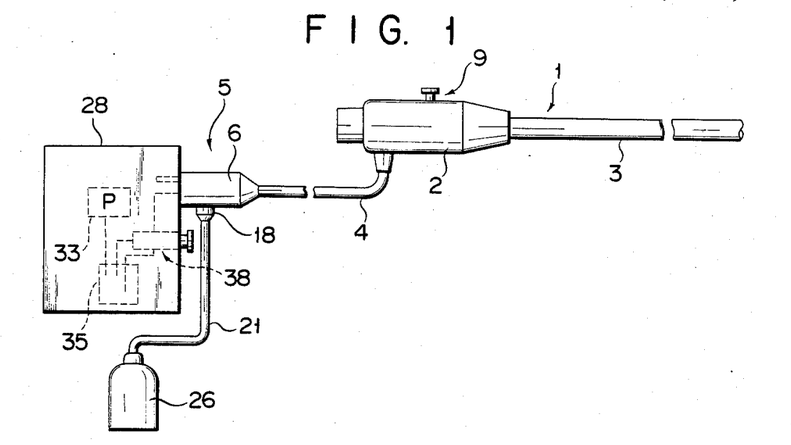
FIG. 1 is a general side view schematically showing the device and an endoscope.

FIG. 1 shows an endoscope 1 and an air and liquid supplying device 5 connected thereto. The endoscope 1 includes an operating section 2 and an insert section 3 extending therefrom. A monitoring window (not shown) is attached to the distal end of the insert section 3. The air and liquid supplying device 5 comprises a housing 28 and a universal cord 4, one end of which is coupled to the operating section 2 of the endoscope 1 and the other end of which is connected to the housing 28 by means of a connector 6.

Inside the endoscope 1, a feed air passage 7 and a feed liquid passage 8 extend from the operating section 2 to the distal end of the insert section 3. The respective lower-course side end portions of the feed air passage 7 and the feed liquid passage 8, i.e., their end portions on the side of the distal end of the insert section 3, join each other and connect with a nozzle 16 at the distal end of the insert section 3. The other ends of the passages 7 and 8 are connected to a first switching valve 9 as first switching means provided in the operating section 2. The first selector valve 9 is connected with an air supply passage 96 which communicates with an air pump 33 (mentioned later) in the housing 28, and with a liquid supply passage 97 which communicates with a first feed liquid tank 26 (mentioned later) outside the housing 28. The air supply passage 96 includes a first portion 96a formed in the operating section 2 and connected to the first selector valve 9, a second portion 96b extending through the universal cord 4 and the connector 6, and a third portion 96c extending in the housing 28 and communicating with the air pump 33. The liquid supply passage 97 includes a first portion 97a which is formed in the operating section 2 and connected to the first selector valve 9, a second portion 97b extending through the universal cord 4 and the connector 6, and a third portion 97c communicating with the first feed liquid tank 26.

Figure 4:
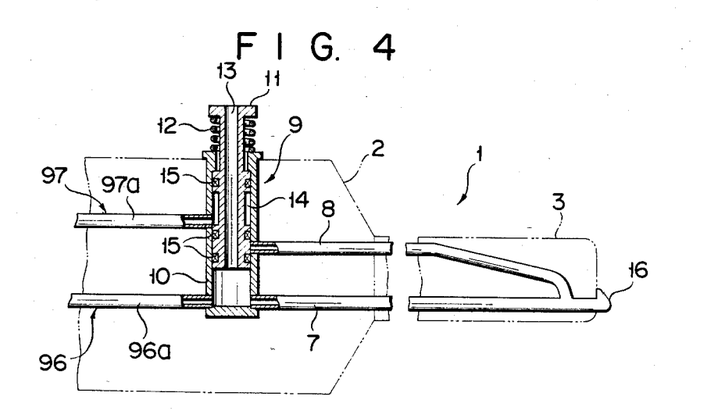
FIG. 4 is a sectional view schematically showing the endoscope.

As shown in FIG. 4, the first selector valve 9 includes a cylinder 10 attached to the operating section 2, a piston 11 slidably fitted in the cylinder 10, and a spring 12 urging the piston 11 in a direction such that the piston 11 projects from the cylinder 10. The upper-course side end of the feed air passage 7 and the lower-course side end of the first portion 96a of the air supply passage 96 are connected to the lower end portion of the peripheral wall of the cylinder 10, while the upper-course side end of the feed liquid passage 8 and the lower-course side end of the first portion 97a of the liquid supply passage 97 are connected to the upper end portion of the peripheral wall of the cylinder 10. A leak hole 13 axially extends through the piston 11, and an annular groove 14 is formed on the outer peripheral surface of the piston 11. When the piston 11 is urged by the spring 12 to project from the cylinder 10, that is, when the piston 11 is located in its first position as shown in FIG. 4, the feed air passage 7 and the air supply passage 96 communicate with each other through the inside space of the cylinder 10, while the feed liquid passage 8 and the liquid supply passage 97 are cut off from each other by the piston 11. If the piston 11 is pushed against the urging force of the spring 12, that is, if the piston 11 is moved to its second position, then the feed air passage 7 is cut off from the air supply passage 96 by the piston 11, and the feed liquid passage 8 and the liquid supply passage 97 are connected by the annular groove 14 of the piston 11. The piston 11 is provided with O-rings 15 for maintaining an airtight relation with the cylinder 10.

Figure 3:
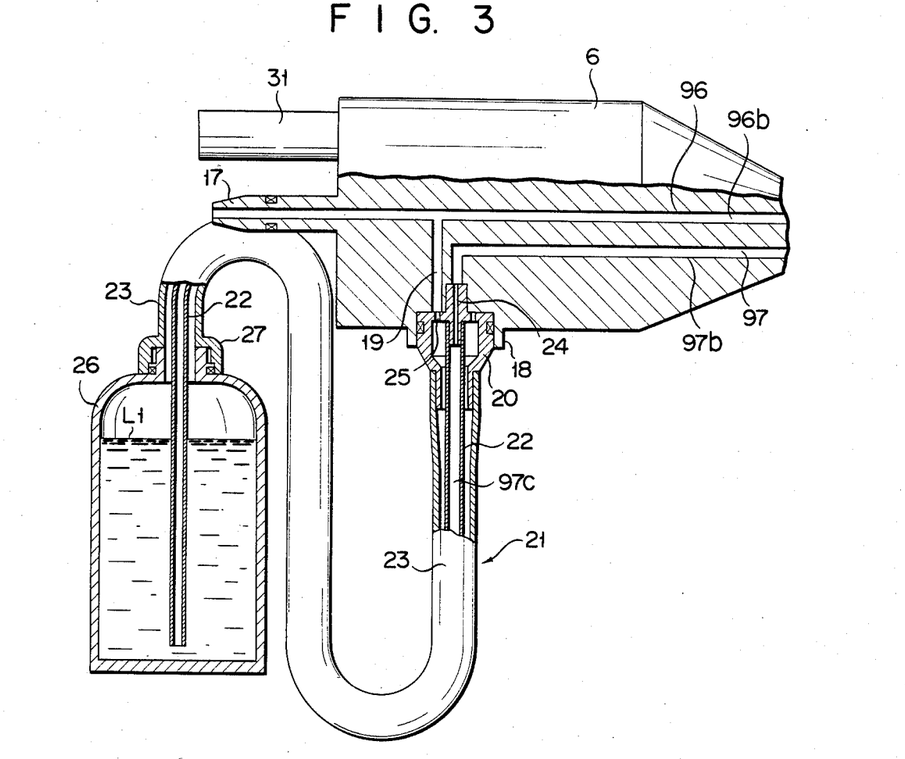

The upper-course side end of the second portion 96b of the air supply passage 96 extending inside the connector 6 opens to the distal end face of a connecting mouthpiece 17 which protrudes from the connector 6. The upper-course side end of the second portion 97b of the liquid supply passage 97 opens to a connecting portion 18 formed on the peripheral surface of the connector 6. A pressurizing passage 19 diverging from the second portion 96b of the air supply passage 96 also opens to the connecting portion 18. A double pipe 21 fitted at one end with a connecting mouthpiece 20 is airtightly connected to the connecting portion 18 by the connecting mouthpiece 20. The double pipe 21 consists of an inner pipe 22 defining the third portion 97c of the liquid supply passage 97, and an outer pipe 23. The inner pipe 22 communicates with a center hole 24 in the connecting mouthpiece 20, while the outer pipe 23 connects with a peripheral hole 25. When the connecting mouthpiece 20 is connected to the connecting portion 18, the inner pipe 22 communicates with the liquid supply passage 97 by means of the center hole 24, and the outer pipe 23 communicates with the pressurizing passage 19 through the peripheral hole 25. The other end of the double pipe 21 is airtightly connected by a cap 27 to a first feed liquid tank 26 which contains a first liquid L1 therein. The outer pipe 23 opens into the upper inside space of the feed liquid tank 26, while the inner pipe 22 is immersed in the liquid L1.

Figure 2:
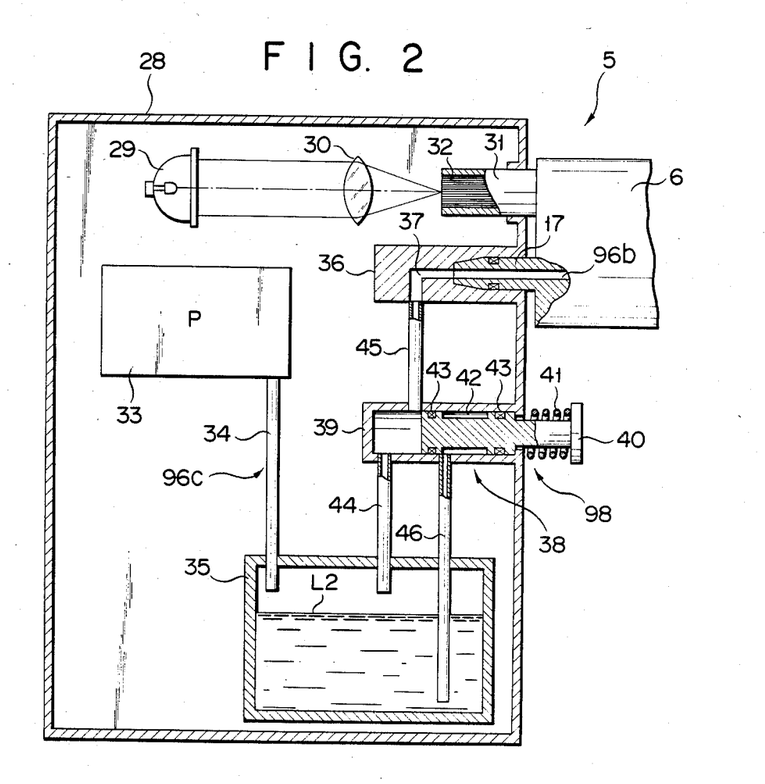
FIGS. 2 and 3 are sectional views showing different sections of the device.

As shown in FIG. 2, a receiving member 36 to be fitted with the connecting mouthpiece 17 of the connector 6 is provided in the housing 28. The receiving member 36 has a communication passage 37 which communicates with the upper-course side end of the second portion 96b of the air supply passage 96. A light source 29 is disposed in the housing 28. A light beam emitted from the light source 29 is converged by a lens 30 and projected on a light guide fiber 32 in a light guide mouthpiece 31 which protrudes from the end face of the connector 6. Also, the air pump 33 and a second feed liquid tank 35 containing a second liquid L2 are arranged in the housing 28. The discharge side of the air pump 33 communicates with the upper inside space of the second feed liquid tank 35 by means of a pressurizing pipe 34. Second switching means 98 including a second selector valve 38 is interposed between the second feed liquid tank 35 and the communication passage 37. The second selector valve 38 includes a cylinder 39, a piston 40 slidably fitted inside the cylinder 39 and having one end portion projecting outside the housing 28, and a spring 41 which urges the piston 40 in a direction such that the piston 40 projects from the cylinder 39. An annular groove 42 is formed on the outer peripheral surface of the piston 40. The piston 40 is provided with O-rings 43 for maintaining an airtight relation with the cylinder 39. The peripheral wall of the cylinder 39 is connected on the bottom side with one end of a first feed air tube 44. The other end of the first feed air tube communicates with the upper inside space of the second feed liquid tank 35. One end of a second feed air tube 45 is connected to the cylinder 39 and the other end is connected to the communication passage 37. One end of a riser tube 46 is connected to the peripheral wall of the cylinder 39. The riser tube 46 is located in a position nearer to the open end of the cylinder 39 than to the feed air tubes 44 and 45. The other end of the riser tube 46 is airtightly inserted in the second feed liquid tank 35 and immersed in the second liquid L2 therein. The communication passage 37, the first and second feed air tubes 44 and 45, and the pressurizing pipe 34 define the third portion 96c of the air supply passage 96. When the second selector valve 38 is in its first position, that is, when the piston 40 is urged by the spring 41 to project from the cylinder 39 as shown in FIG. 2, the first and second feed air tubes 44 and 45 communicate with each other by means of the inside space of the cylinder 39. If the piston 40 is pushed into its second position, the riser tube 46 and the second feed air tube 45 communicate with each other by the annular groove 42 of the piston 40.

The operation of the air and liquid supplying device 5 with the aforementioned construction will now be described. When using the endoscope 1 for ordinary observation or the like, the air pump 33 is actuated without operating the first and second selector valves 9 and 38, as shown in FIGS. 4 and 2. Thereupon, air from the air pump 33 flows into the first and second portions 96a and 96b of the air supply passage 96 via the pressurizing pipe 34, the upper inside space of the second feed liquid tank 35, the first feed air tube 44, the inside space of the cylinder 39 of the second selector valve 38, the second feed air tube 45, and the communication passage 37. The air delivered to the lower-course side of the air supply passage 96 is discharged into the outside air through the leak hole 13 of the piston 11 of the first selector valve 9. Therefore, if the leak hole 13 is closed by a finger, the air jets from the nozzle 16, passing through the feed air passage 7. In feeding a liquid into the feed liquid passage 7, the piston 11 of the first selector valve 9 is pushed into its second position cutting off the feed air passage 7 from the air supply passage 96, and thus connecting the feed liquid passage 8 and the liquid supply passage 97. When the feed air passage 7 is cut off, air introduced into the air supply passage 96 flows into the first feed liquid tank 26 through the pressurizing passage 19 and the outer pipe 23 of the double pipe 21, thereby pressurizing the liquid L1 in the tank 26. As a result, the liquid L1 flows into the liquid supply passage 97 through the inner pipe 22 of the double pipe 21. Thereafter, it flows into the feed liquid passage 8 through the annular groove 14 of the piston 11 of the first selector valve 9, and gushes from the nozzle 16.

After the use of the endoscope 1 is ended, the piston 40 of the second selector valve 38 is pushed into its second position while keeping the air pump 33 in operation, thereby cutting off the first feed air tube 44 from the second feed air tube 45, and connecting the second feed air tube 45 and the riser tube 46. As a result, the liquid L2 is pressurized by the air fed from the air pump 33 into the second feed liquid tank 35, and flows to the lower-course side of the air supply passage 96 through the riser tube 46, the second feed air tube 45, and the communication passage 37. Therefore, if the leak hole 13 of the piston 11 of the first selector valve 9 is closed, the liquid L2 passes through the feed air passage 7 and flows out from the nozzle 16. Thus, the feed air passage 7 is washed throughout the its length by the flow of the liquid L2. If disinfectant is used for the second liquid L2, then the feed air passage 7 will be disinfected.

The liquid L2 remaining in the feed air passage 7 can be removed by feeding air into the passage 7 in the aforesaid manner after thus washing the passage 7.

With this arrangement, the liquid can be fed into the feed air passage 7, so that normal observation can satisfactorily be achieved by cleaning the monitering window by the use of the feed air passage 7 even if the feed liquid passage 8 is clogged.

Figure 5:
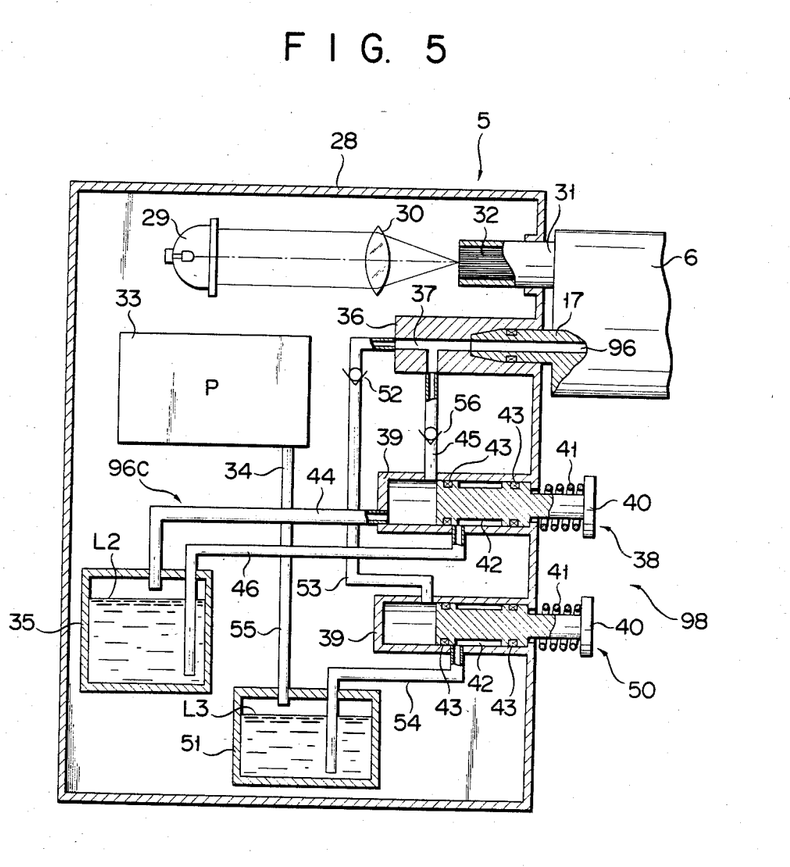
FIG. 5 is a sectional view showing the principal parts of an air and liquid supplying device according to a second embodiment of the invention.

FIG. 5 shows a second embodiment of the present invention. In this embodiment, a third selector valve 50 with the same construction as the second selector valve 38 is additionally provided as the second switching means 98 in the housing 28. Also, a third feed liquid tank 51 containing a third liquid L3 is diposed in the housing 28. The third selector valve 50 is provided with a feed liquid tube 53 one end of which is connected to the peripheral wall of its cylinder 39 and the other end of which is connected to the communication passage 37 of the receiving member 36 through a first check valve 52. A second riser tube 54 is connected at one end to the peripheral wall of the cylinder 39 and is immersed at the other end in the liquid L3 in the third feed liquid tank 51. A pressurizing branch pipe 55 diverging from the pressurizing pipe 34 is connected to the third feed liquid tank 51 to communicate with the upper inside space thereof. The second feed air tube 45 is provided with a second check valve 56.

With this arrangement, the liquid L2 in the second feed liquid tank 35 can be passed through the feed air passage 7 in the same manner as in the first embodiment by operating the second selector valve 38. If the piston 40 of the third selector valve 50 is pushed into its second position to connect the feed liquid tube 53 and the second riser tube 54 by means of the annular groove 42 of the piston 40, while keeping the piston 40 of the second selector valve 38 in its second position, then the liquid L3 in the third feed liquid tank 51, which has been pressurized by the air from the pressurizing branch pipe 55, flow through the feed air passage 7. Thus, only the second liquid L2 in the second feed liquid tank 35, or both of the second and third liquids L2 and L3 can be passed through the feed air passage 7 at the same time. Therefore, if a lotion and an antiseptic are used for the second and third liquids L2 and L3, the feed air passage 7 may be washed and disinfected by passing a mixture of the two liquids L2 and L3 through it. Any antiseptic used as the third liquid L3 which remains in the feed air passage 7 can be removed by passing only the lotion through the passage 7. Thus, the lotion and/or antiseptic may be selectively passed through the feed air passage 7.

Figure 6:
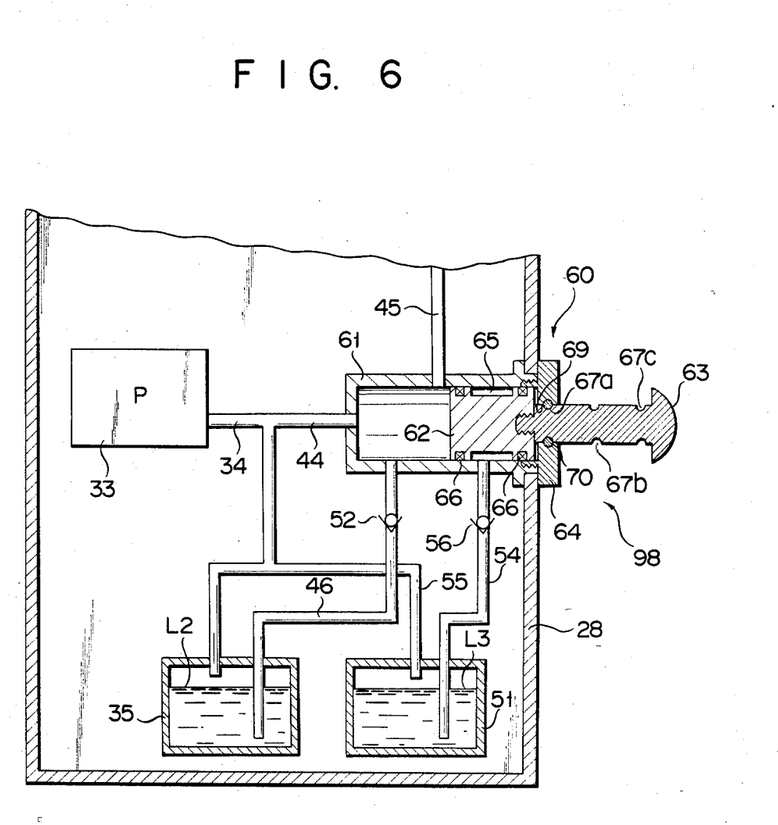
FIG. 6 is a sectional view showing the principal parts of an air and liquid supplying device according to a third embodiment of the invention.

FIG. 6 shows a third embodiment of the present invention. In this embodiment, a fourth selector valve 60 of a three-stage shift type is used as the second switching means 98 which replaces the second and third selector valves 38 and 50 used in the second embodiment. The fourth selector valve 60 includes a cylinder 61 fixed to the housing 28, a piston 62 slidably fitted in the cylinder 61, an operating rod 63 coupled to the piston 62 and projecting from the cylinder 61, and a cover 64 closing the opening of the cylinder 61. An annular groove 65 is formed on the outer peripheral surface of the piston 62, and O-rings 66 are put on the piston 62 in an airtight relation with the cylinder 61. First, second and third annular engaging grooves 67a, 67b and 67c are formed on the outer peripheral surface of the operating rod 63 along the axis of the rod 63. These engaging grooves 67a, 67b and 67c successively elastically engage an O-ring 70 on the inner peripheral surface of a hole 69 in the cover 64 when the operating rod 63 is pushed into the cylinder 61. One end of the feed air tube 45, the other end of which connects with the communication passage 37 of the connector 6, is connected at the halfway point of the peripheral wall of the cylinder 61. One end of the riser tube 46, the other end of which is immersed in the liquid L2 in the second feed liquid tank 35, is connected to the peripheral wall of the cylinder 61 near the bottom portion thereof through the first check valve 52. Likewise, one end of the second riser tube 54, the other end of which is immersed in the liquid L3 in the third feed liquid tank 51, is connected to the peripheral wall of the cylinder 61 near the top portion thereof through the second check valve 56. When the piston 62 is pulled up in the cylinder 61 to take its first position where the first engaging groove 67a of the operating rod 63 engages the O-ring 70, as shown in FIG. 6, the pressurizing pipe 34 communicates with the feed air tube 45 by means of the inside space of the cylinder 61. When the piston 62 is pushed into its second position where the second engaging groove 67b engages the O-ring 70, the feed air tube 45 communicates with the second riser tube 54 by means of the annular groove 65. When the piston 62 is pushed into its third position where the third engaging groove 67c engages the O-ring 70, the feed air tube 45 communicates with the riser tube 46 by means of the annular groove 65.

By using the fourth selector valve 60 constructed in this manner, the liquid L3 in the third feed liquid tank 51 may be fed into the feed air passage 7 by operating the piston 62 so that the feed air tube 45 communicates with the second riser tube 54. Further, the liquid L2 in the second feed liquid tank 35 may be passed through the feed air passage 7 by connecting the feed air tube 45 and the riser tube 46. Thus, the liquid L2 or L3 may selectively be fed into the feed air passage 7.

According to this third embodiment, moreover, the liquid L3 or a mixture of the two liquids L2 and L3 may selectively be fed into the feed air passage 7 by setting the length of the annular groove 65 so that both the first and second riser tubes 46 and 54 communicate with the feed air tube 45 when the piston 62 is pushed into the third position where the third engaging groove 67c of the operating rod engages the O-ring 70.

Figure 7:
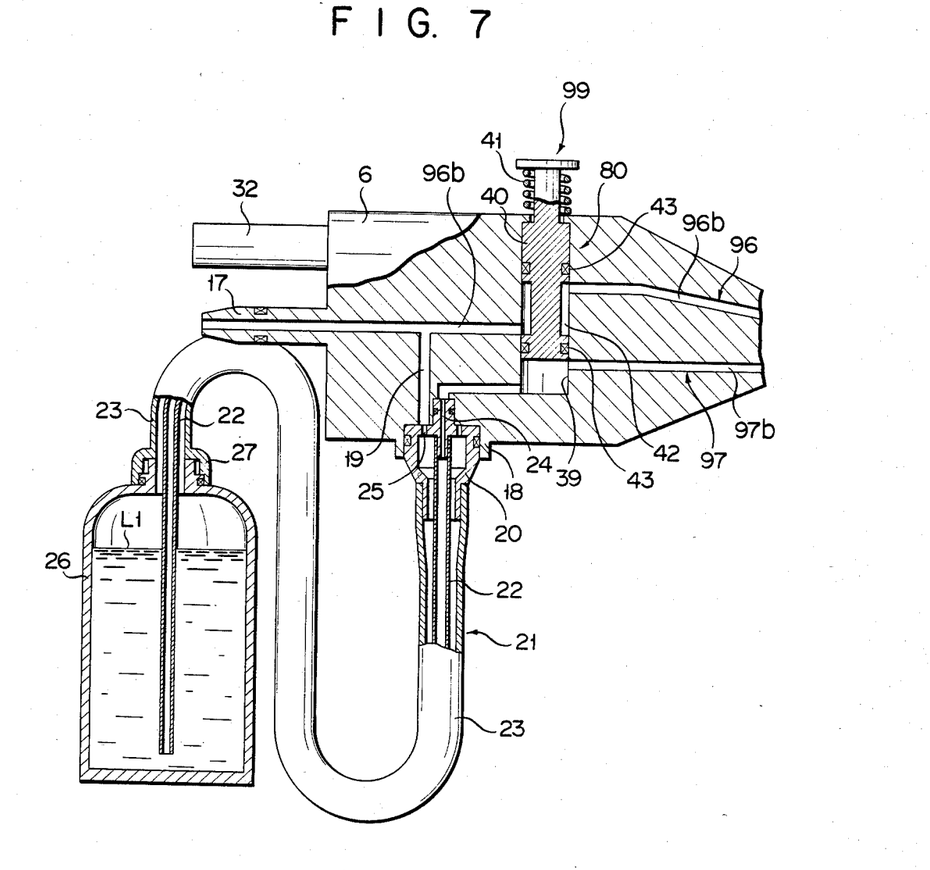
FIG. 7 is a sectional view of a connector section in an air and liquid supplying device according to a fourth embodiment of the invention.

FIG. 7 shows a fourth embodiment of the present invention. This embodiment is substantially the same as the first embodiment shown in FIGS. 1 to 4, except that it is further provided with a fifth selector valve 80 as third switching means on the connector 6. The fifth selector valve 80 has the same construction as that of the second selector valve 38 used in the first embodiment. Therefore, like reference numerals are used to designate like portions of the valve to avoid repeated description. The cylinder 39 of the fifth selector valve 80 is provided in the middle of the respective second portions 96b and 97b of the air supply passage 96 and the liquid supply passage 97. When the piston 40 of the fifth selector valve 80 is in its first position where it projects from the cylinder 39, the air supply passage 96 and the liquid supply passage 97 are opened by means of the annular groove 42 of the piston 40 and the inside space of the cylinder 39, respectively. When the piston 40 is pushed into its second position, the lower-course side of the second portion 96b of the air supply passage 96 and the upper-course side of the second portion 97b of the liquid supply passage 97 are cut off by the piston 40, while the upper-course side of the second portion 96b of the air supply passage 96 and the lower-course side of the second portion 97b of the liquid supply passage 97 are connected by the annular groove 42.

According to this arrangement, without operating the fifth selector valve 80, air or liquid may be fed into the feed air passage 7 by operating the second selector valve 38 in the same manner as in the first embodiment. If the piston 40 of the fifth selector valve 80 is pushed into its second position when the second selector valve 38 is in the position for air feed, then the upper-course side of the second portion 97b of the liquid supply passage 97 is cut off, and the upper-course side of the second portion 96b of the air supply passage 96 and the lower-course side of the second portion 97b of the liquid supply passage 97 are connected. Thus, air may be fed into the feed liquid passage 8 to drain off the liquid therefrom. If the piston 40 of the fifth selector valve 80 is pushed in when the second selector valve 38 is in its second position for liquid feed, then the liquid L2 in the second feed liquid tank 35 may be passed through the feed liquid passage 8. Thus, the feed liquid passage 8 can be disinfected by using an antiseptic solution for the liquid L2.

The fifth selector valve 80 of the fourth embodiment may be used in combination with the device of the second embodiment shown in FIG. 5. With this arrangement, the liquid L2 in the second feed liquid tank 35, or a mixture of the liquid L3 in the third feed liquid tank 51 and the liquid L2 may selectively be fed into the feed liquid passage 8.

Figure 8:
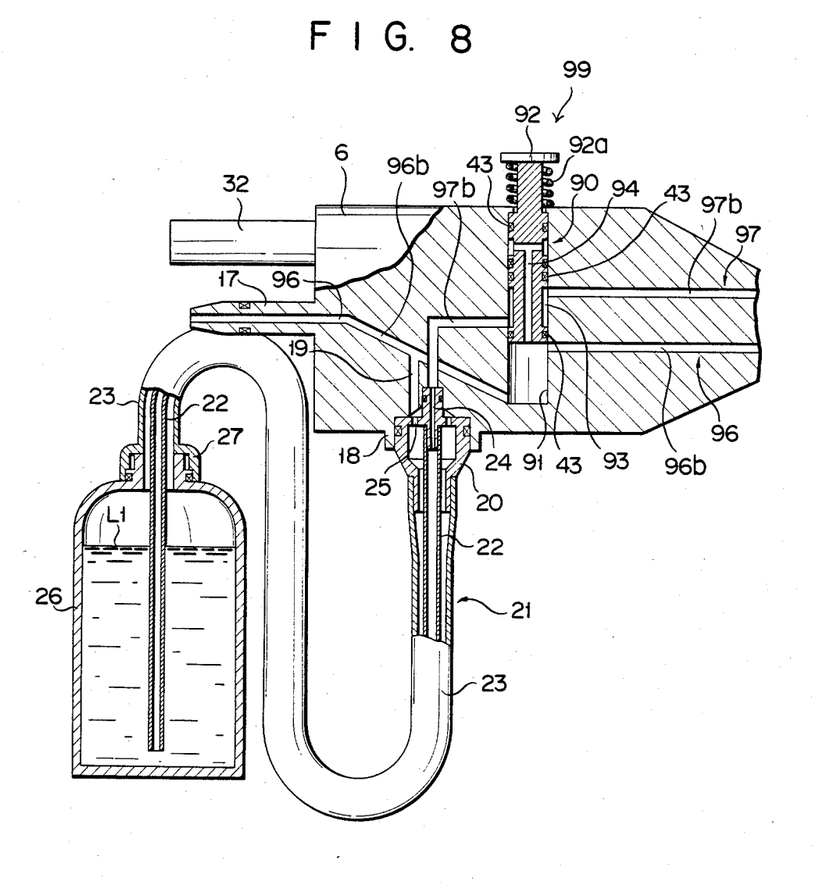
FIG. 8 is a sectional view of a connector section in an air and liquid supplying device according to a fifth embodiment of the invention.

FIG. 8 shows a fifth embodiment of the present invention. This embodiment is substantially the same as the fourth embodiment shown in FIG. 7, except that it is provided with a sixth selector valve 90 of a two-stage shift type in place of the fifth selector valve 80 as the third switching means 99. The sixth selector valve 90 includes a cylinder 91 formed in the connector 6, a piston 92 slidably fitted in the cylinder 91, and a spring 92a urging the piston 92 in a direction such that the piston 92 projects from the cylinder 91. An annular groove 93 is formed on the outer peripheral surface of the piston 92. The piston 92 has therein a T-shaped communication passage 94, one end of which opens to the bottom end face of the piston 92 and the other two ends of which open to the outer peripheral surface of the piston 92 above the annular groove 93. The cylinder 91 is located in the middle of the respective second portions 96b and 97b of the air supply passage 96 and the liquid supply passage 97. When the piston 92 is located in its first position, as shown in FIG. 8, the second portions 96b and 97b of the air supply passage 96 and the liquid supply passage 97 are opened by means of the inside space of the cylinder 91 and the annular groove 93 of the piston 92, respectively. When the piston 92 is pushed in for one stage, the upper-course side of the air supply passage 96 is cut off by the piston 92, and the upper-course side of the liquid supply passage 97 and the lower-course side of the air supply passage 96 are connected by the annular groove 93. When the piston 92 is pushed in for the other stage, the upper-course side of the air supply passage 96 and the lower-course side of the liquid supply passage 97 are connected by the communication passage 94 in the piston 92, and the upper-course side of the liquid supply passage 97 and the lower-course side of the air supply passage 96 are connected by the annular groove 93.

According to this arrangement, without operating the sixth selector valve 90, air or liquid may be fed into the feed air passage 7 by operating the second selector valve 38. If the piston 92 of the sixth selector valve 90 is pushed in for one state when the second selector valve 38 is in the position for air feed, then the upper-course side of the air supply passage 96 is cut off, so that the air from the air pump 33 flows into the first feed liquid tank 35 through the pressurizing passage 19 and the double pipe 21, thereby pressurizing the liquid L1. As a result, the liquid L1 flows to the lower-course side of the air supply passage 96 via the annular groove 93. Thus, if the leak hole 13 of the first relector valve 9 closed by a finger, the feed air passage 7 can be washed by the liquid L1. If the piston 92 is pushed in for the second stage, the upper-course side of the air supply passage 96 and the lower-course side of the liquid supply passage 97 are connected by the communication passage 94. Thus, air is fed into the feed liquid passage 8 to remove any liquid L1 remaining therein.

If the piston 92 of the sixth selector valve 92 is pushed in for the two stages when the second selector valve 38 is in its second position for liquid feed, then the liquid L2 from the second feed liquid tank 35 which is delivered to the upper-course side of the air supply passage 96 can be fed to the lower-course side of the liquid supply passage 97 through the communication passage 94 of the piston 92. Thus, the feed liquid passage 8 can be disinfected by using an antiseptic solution for the liquid L2.

According to the arrangement described above, air and liquid may be fed individually into the feed air passage 7 and into the feed liquid passage 8. Liquid L2 in the second feed liquid tank 35 can be passed through the feed liquid passage 8.

It is to be understood that the present invention is not limited to the above-mentioned embodiments, and that various changes and modifications may be effected therein by one skilled in the art without departing from the scope or spirit of the invention. For example, the first switching means may be attached to any other suitable portion, such as the connector 6, than the operating section of the endoscope. Also, the third switching means may be attached to the operating section of the endoscope.

What is claimed is:

1. An air and liquid supplying device for an endoscope which includes an operating section, an insert section extending from the operating section, and a feed air passage and a feed liquid passage extending from the operating section to the distal end of the insert section, said device comprising;:
   an air pump;
   a first feed liquid tank containing a first liquid;
   first switching means connected to the feed air passage and the feed liquid passage;
   connecting means including an air supply passage connecting the pump and the first switching means, a pressurizing passage diverging from the air supply passage and communicating with the first feed liquid tank, and a liquid supply passage containing the first feed liquid tank and the first switching means, said first switching means being capable of being shifted between a first position where the air supply passage and the feed air passage are connected so that air from the pump is fed into the feed air passage, and a second position where the feed air passage is cut off and the liquid supply passage and the feed liquid passage are connected so that the first liquid is fed into the feed liquid passage;
   a second feed liquid tank containing a second liquid and connected to the air supply passage between the pump and the pressurizing passage; and
   second switching means connected to the air supply passage between the second feed liquid tank and the pressurizing passage, and adapted to switch the device to supply air to the air supply passage and to supply the second liquid to the air supply passage.

2. A device according to claim 1, wherein said second switching means includes a second selector valve and a riser tube one end of which is immersed in the second liquid in the second feed liquid tank and the other end of which is connected to the second selector valve, said second selector valve being capable of being shifted between a first position where the air from the air pump is fed into the air supply passage, and a second position where the air supply passage and the riser tube are connected so that the second liquid is fed into the air supply passage.

3. A device according to claim 2, wherein said second selector valve includes a cylinder, a piston having an annular groove on the outer peripheral surface thereof and slidably fitted in the cylinder, and urging means urging the piston in a direction such that the piston projects from the cylinder, and the air supply passage and the other end of the riser tube communicate with the interior of the cylinder, the piston being adapted to close the riser tube and open the air supply passage when the second selector valve is in the first position thereof, and to close the upper-course side of the air supply passage and connect the riser tube and the lower-course side of the air supply passage by means of the annular groove when the second selector valve is in the second position thereof.

4. A device according to claim 1, wherein said first switching means includes a first selector valve having a cylinder connected with the respective lower-course side ends of the air supply passage and the liquid supply passage and with the respective upper-course side ends of the feed air passage and the feed liquid passage, a piston having an annular groove on the outer peripheral surface thereof and slidably fitted in the cylinder, and urging means urging the piston in a direction such that the piston projects from the cylinder, the piston being capable of being shifted between a first position where the air supply passage and the feed air passage are connected, and a second position where the air supply passage is closed and the liquid supply passage and the feed liquid passage are connected by means of the annular groove.

5. A device according to claim 4, wherein said cylinder of the first selector valve is attached to the operating section of the endoscope.

6. A device according to claim 1, which further comprises a third feed liquid tank containing a third liquid, and characterized in that said second switching means includes a pressurizing branch tube connecting the third feed liquid tank and the air supply passage, a third selector valve, a riser tube one end of which is connected to the third selector valve and the other end of which is immersed in the third liquid in the third feed liquid tank, and a feed liquid tube one end of which is connected to the third selector valve and the other end of which is connected to the air supply passage between the second selector valve and the pressurizing passage, the third selector valve being capable of being shifted between a first position where the riser tube is closed and a second position where the riser tube and the feed liquid tube are connected to allow the supply of the third liquid to the air supply passage.

7. A device according to claim 1, which further comprises a third feed liquid tank containing a third liquid, and characterized in that said second switching means includes a selector valve, a first riser tube one end of which is connected to the selector valve and the other end of which is immersed in the second liquid in the second feed liquid tank, a pressurizing branch tube connecting the third feed liquid tank and the air supply passage, and a second riser tube one end of which is connected to the selector valve and the other end of which is immersed in the third liquid in the third feed liquid tank, the selector valve being capable of being shifted between a first position where the second riser tube is closed and the air supply passage is opened, a second position where the upper-course side of the air supply passage and the first riser tube are closed and the lower-course side of the air supply passage and the second riser tube are connected to allow the supply of the third liquid to the air supply passage, and a third position where the upper-course side of the air supply passage and the second riser tube are closed and the lower-course side of the air supply passage and the first riser tube are connected to allow the supply of the second liquid to the air supply passage.

8. A device according to claim 1, which further comprises third switching means connected to the air supply passage and the liquid supply passage between the first switching means and the pressurizing passage, and capable of being shifted between a first position where the air supply passage and the liquid supply passage are opened and a second position where the lower-course side of the air supply passage and the upper-course side of the liquid supply passage are closed and the upper-course side of the air supply passage and the lower-course side of the liquid supply passage are connected to allow the supply of the second liquid or air to the feed liquid passage.

9. A device according to claim 8, wherein said third switching means comprises a selector valve including a cylinder connected to the air supply passage and the liquid supply passage, a piston having an annular groove on the outer peripheral surface thereof and slidably fitted in the cylinder, and urging means urging the piston in a direction such that the piston projects from the cylinder, the piston being adapted to open the air supply passage and the liquid supply passage by means of the inside space of the cylinder and the annular groove, respectively, when the third switching means is in the first position thereof, and to close the lower-course side of the air supply passage and the upper-course side of the liquid supply passage and connect the upper-course side of the air supply passage and the lower-course side of the liquid supply passage by means of the annular groove when the third switching means is in the second position thereof.

10. A device according to claim 1, which further comprises third switching means connected to the air supply passage and the liquid supply passage between the first switching means and the pressurizing passage, and capable of being shifted between a first position where the air supply passage and the liquid supply passage are opened, a second position where the upper-course side of the air supply passage and the lower-course side of the liquid supply passage are closed and the upper-course side of the liquid supply passage and the lower-course side of the air supply passage are connected to allow the supply of the first liquid to the feed air passage, and a third position where the upper-course side of the liquid supply passage and the lower-course side of the air supply passage are connected and the upper-course side of the air supply passage and the lower-course side of the liquid supply passage are connected to allow the supply of the second liquid or air to the feed liquid passage.

11. A device according to claim 10, wherein said third switching means comprises a selector valve including a cylinder connected to the air supply passage and the liquid supply passage, a piston slidably fitted in the cylinder and having an annular groove on the outer peripheral surface thereof and a substantially T-shaped communication passage one end of which opens to the bottom face of the piston and the other ends of which open to the peripheral surface of the piston, and urging means which urges the piston in a direction such that the piston projects from the cylinder, the piston being adapted to open the air supply passage and the liquid supply passage by means of the inside space of the cylinder and the annular groove, respectively, when the third switching means is in the first position thereof, to close the upper-course side of the air supply passage and the lower-course side of the liquid supply passage and to connect the upper-course side of the liquid supply passage and the lower-course side of the air supply passage by means of the annular groove when the third switching means is in the second position thereof, and to connect the upper-course side of the liquid supply passage and the lower-course side of the air supply passage and to connect the upper-course side of the air supply passage and the lower-course side of the liquid supply passage by means of the communication passage when the third switching means is in the third position thereof.

* * * * *